(12) United States Patent
    Jinks (10) Patent No.: US 10,029,845 B2
(45) Date of Patent: Jul. 24, 2018

(54) METERED DOSE INHALERS

(71) Applicant: 3M INNOVATIVE PROPERTIES COMPANY, St. Paul, MN (US)

(72) Inventor: Philip A. Jinks, Loughborough (GB)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/552,401

(22) PCT Filed: Feb. 22, 2016

(86) PCT No.: PCT/US2016/018848
§ 371 (c)(1),
(2) Date: Aug. 21, 2017

(87) PCT Pub. No.: WO2016/137853
PCT Pub. Date: Sep. 1, 2016

(65) Prior Publication Data
US 2018/0057248 A1    Mar. 1, 2018

(30) Foreign Application Priority Data
Feb. 27, 2015  (GB) .................................. 1503402.8

(51) Int. Cl.
  *B65D 83/14*  (2006.01)
  *B65D 83/54*  (2006.01)
  (Continued)

(52) U.S. Cl.
  CPC ......... *B65D 83/546* (2013.01); *A61M 15/009* (2013.01); *G01F 11/14* (2013.01);
  (Continued)

(58) Field of Classification Search
  CPC .... B65D 83/54; B65D 83/546; A61M 15/009; G01F 11/14; F16K 7/12; F16K 31/1268
  See application file for complete search history.

(56) References Cited

U.S. PATENT DOCUMENTS

| 3,756,474 | A | * | 9/1973 | Riccio | ..................... B05B 11/06 |
| | | | | | 222/635 |
| 4,135,648 | A | * | 1/1979 | White | ..................... B65D 83/54 |
| | | | | | 222/402.2 |
| 4,819,834 | A | | 4/1989 | Thiel | |
| 4,919,312 | A | * | 4/1990 | Beard | ..................... B65D 83/54 |
| | | | | | 222/107 |

(Continued)

FOREIGN PATENT DOCUMENTS

| GB | 2 206 860 | 1/1989 |
| GB | 2 345 279 | 7/2000 |

(Continued)

*Primary Examiner* — Frederick C Nicolas (57) ABSTRACT

The present invention addresses the problem of turbophoresis and provides a relatively simple and low cost solution for a metered dose inhaler, in particular, a pressure-actuated metered dose inhaler. A metering valve (100) comprises a valve body (110), a valve stem (130) mounted within the valve body (110) and a spring element (140) for biasing the valve stem (130) in an "at rest" position. A pre-metering region (170) is formed in the valve stem (130) which is provided with a miniature valve seal (210) at its inlet (180). The miniature valve seal (210) effectively isolates the pre-metering region (170) from surrounding bulk formulation (4) within a canister (1) in which the metering valve (100) is mounted when the valve stem (130) is in the "at rest" position.

17 Claims, 8 Drawing Sheets

(51) Int. Cl.
*A61M 15/00* (2006.01)
*G01F 11/14* (2006.01)
*F16K 31/126* (2006.01)
*F16K 7/12* (2006.01)

(52) U.S. Cl.
CPC ............... *B65D 83/54* (2013.01); *F16K 7/12* (2013.01); *F16K 31/1268* (2013.01)

(56) References Cited

U.S. PATENT DOCUMENTS

| | | | | |
|---|---|---|---|---|
| 5,593,069 A | * | 1/1997 | Jinks | B65D 83/54 |
| | | | | 222/246 |
| 6,454,140 B1 | * | 9/2002 | Jinks | B65D 83/54 |
| | | | | 222/402.2 |
| 6,644,306 B1 | * | 11/2003 | Riebe | A61M 15/009 |
| | | | | 128/200.14 |
| 2006/0124903 A1 | * | 6/2006 | Ito | A61K 9/008 |
| | | | | 252/372 |
| 2007/0131722 A1 | * | 6/2007 | Goujon | B65D 83/54 |
| | | | | 222/402.2 |
| 2007/0145081 A1 | * | 6/2007 | Goujon | B65D 83/54 |
| | | | | 222/402.2 |
| 2008/0087688 A1 | * | 4/2008 | Twyman | B65D 83/54 |
| | | | | 222/402.2 |

FOREIGN PATENT DOCUMENTS

| | | |
|---|---|---|
| GB | 2 474 360 | 4/2011 |
| WO | 2002/10037 | 2/2002 |

\* cited by examiner

METERED DOSE INHALERS

CROSS REFERENCE TO RELATED APPLICATIONS

This application is a national stage filing under 35 U.S.C. § 371 of PCT/US2016/018848, filed 22 Feb. 2016, which claims the benefit of United Kingdom Application No. 1503402.8, filed 27 Feb. 2015, the disclosures of which are incorporated by reference in their entirety herein.

TECHNICAL FIELD OF THE INVENTION

The present invention relates to improvements in or relating to metered dose inhalers, and is more particularly concerned with pressure-actuated metered dose inhaler devices.

BACKGROUND OF THE INVENTION

Pressure-actuated metered dose inhaler (pMDI) devices are designed to dispense a predetermined dose of a medicament to a user or patient when actuated. The medicament is stored and dispensed either as a fluid of active particles in a suspension or with the active agent dissolved in the fluid. The operation of a valve within the device is used to dispense the dose of medicament from a metering region once the device is activated. However, dosing variation, that is, dose enrichment or dose depletion, may be experienced when particles in the suspension migrate in the direction of decreasing fluid turbulence (which can be into or out of the metering chamber), resulting in variations in the actual dose of the medicament dispensed to the patient. This migration is a phenomenon known as turbophoresis.

WO-A-02/10037 describes ways of closing off a valve metering chamber when the pMDI device is at rest in order to prevent dose enrichment or dose depletion effects directly into or out of the metering chamber. However, dose enrichment or dose depletion effects occurring in a critical pre-metering region of the valve are not addressed so that, even when the metering chamber is closed off at rest, dose enrichment or dose depletion can still occur due to particles migrating into or out of the pre-metering region. This means that a patient may not always take the correct dose of his/her medicament due to no fault of his/her own.

SUMMARY OF THE INVENTION

It is an object of the present invention to provide an improved pressure-actuated metered dose inhaler device in which the effects of turbophoresis are at least substantially reduced.

It is another object to provide a simple but effect way of substantially reducing the effects of turbophoresis at low cost.

In accordance with one aspect of the present invention, there is provided a metering valve comprising:—
  a housing;
  a valve body mounted in the housing, the valve body having an inlet;
  a valve stem moveable within the valve body between at least a first position and a second position with respect to the valve body;
  a return member located within the valve body and being operable for biasing the valve stem to the first position;
  a pre-metering region formed within a first portion of the valve stem, the pre-metering region including an inlet port and an outlet port, the inlet port being connected to the inlet of the valve body;
  a metering chamber formed between the valve stem and the valve housing, the metering chamber being connectable to the outlet port of the pre-metering region;
  a first dose retention element positioned in an inlet path to the pre-metering region and being operable for retaining a measured dose within the pre-metering region, the first dose retention element providing fluid transport in both directions therethrough; and
  a dispensing channel formed within a second portion of the valve stem, the dispensing channel having a dispensing inlet and a dispensing outlet, the dispensing inlet being connectable to the metering chamber in the second position.

By providing the first dose retention element in an inlet path to the pre-metering region, the phenomenon of turbophoresis can at least be substantially reduced resulting in the ability to dispense metered doses which are not dose depleted or dose enriched due to the migration of active particles into and out of the pre-metering region.

The first dose retention element acts as a valve seal trapping active particles of a medicament within the pre-metering region and the metering chamber prior to activation of the valve for dispensing the medicament to a patient. In addition, the first dose retention element effectively isolates the pre-metering region from bulk formulation surrounding the metering valve in a pressure-activated metered dose inhaler device.

In one embodiment, the first dose retention member is located at an entrance to the pre-metering region, the entrance being substantially adjacent the inlet port.

By locating the first dose retention member at the entrance to the pre-metering region, assembly of the metering valve is relatively simple as the first does retention member can readily be fixed to the entrance to the pre-metering region in the valve stem.

The outlet port preferably comprises an opening in a circumferential wall of the valve stem.

In one embodiment, the inlet port comprises an opening at a proximal end of the valve stem. In this embodiment, the first dose retention member may have an axis which is substantially aligned with the inlet port. In other embodiments, the first dose retention member may have an axis which is substantially aligned with the outlet port. Naturally, the alignment of the first dose retention member will depend on the particular configuration of the metering valve.

In one embodiment, the inlet port comprises an opening in a circumferential wall of the valve stem disposed at a distance from the outlet port. In one embodiment, the first dose retention member may have an axis which is substantially aligned with the inlet port. In other embodiments, the first dose retention member may have an axis which is substantially aligned with the outlet port. The alignment of the first dose retention member will be in accordance with the configuration of the metering valve.

The first dose retention member may comprise an elastomeric disc with at least one re-sealable slit located in a central region thereof.

By having an elastomeric disc as the first dose retention member, it can be flexed to be inserted into an appropriate location within the valve stem, either in the input path of or at the entrance to the pre-metering region.

In one embodiment, the elastomeric disc has a circumferential region which is thicker than the central region thereof. This has the advantage of making the elastomeric disc easier to handle. Ideally, the elastomeric disc is symmetrical, that is, it has no top or bottom, allowing it to be readily insertable, with less sophisticated assembly equipment, into the valve stem in the input path of or at the entrance to the pre-metering region. The elastomeric disc may be moulded from an elastomer or a thermoplastic elastomer. Preferably, the re-sealable slit is provided by cutting the moulded article with a narrow blade.

In another embodiment, a second dose retention member is positioned in an outlet path of the pre-metering region. In one embodiment, the second dose retention member is located at an exit to the pre-metering region. In each case, the second dose second retention member may have an axis which is substantially aligned with the outlet port.

By providing a second dose retention member in the outlet path from or at the exit to the pre-metering region, the pre-metering region can effectively be isolated from both the bulk formulation and from the metering chamber. This isolation also assists in the reduction of the effects of turbophoresis.

The second dose retention member comprises an elastomeric disc with at least one re-sealable slit located in a central region thereof. In one embodiment, the elastomeric disc has a circumferential region which is thicker than the central region thereof. Preferably, the second dose retention member is substantially identical to the first dose retention member.

By having identical dose retention members, they are interchangeable resulting in ease of assembly of the metering valve. In addition, the dose retention members can readily be assembled in the metering valve irrespective of their orientation as they may be symmetrical top and bottom.

BRIEF DESCRIPTION OF THE DRAWINGS

For a better understanding of the present invention, reference will now be made, by way of example, to the accompanying drawings in which:—

DESCRIPTION OF THE INVENTION

The present invention will be described with respect to particular embodiments and with reference to certain drawings but the invention is not limited thereto. The drawings described are only schematic and are non-limiting. In the drawings, the size of some of the elements may be exaggerated and not drawn on scale for illustrative purposes.

In accordance with the present invention, it has been determined that the positioning of a miniature valve seal at the inlet to the pre-metering region of a pMDI device substantially reduces, and in some cases, prevents turbophoresis effects.

For a better understanding of the potential effects of turbophoresis and how to prevent such effects, a discussion of the operation of a pMDI device is provided. The valve of the pMDI device has a metering region and a pre-metering region, the pre-metering region being a low turbulence region in direct fluid contact with the bulk formulation which is a high turbulence region. Any fluid movement has the potential to cause migration of particles from the bulk formulation to the pre-metering region. Once the particles have entered the pre-metering region, they are effectively trapped there because shaking of the pMDI device does not empty the pre-metering region. The enriched pre-metering region then empties its enriched contents into the metering chamber on the next valve refilling cycle thereby providing an enriched dose for the patient.

The present invention as described herein relates to pMDI valves featuring a shut-off miniature valve seal or dose retention element located in the inlet path or at the entrance to the pre-metering region of the valve. The miniature valve seal may comprise a simple elastomeric disc including at least one slit in a central region thereof which can readily be located in position, for example, by push fitting or welding.

The elastomeric disc may be substantially symmetrical so that it can readily be inserted into its correct position without having to determine a particular orientation. The central region of the elastomeric disc may have a single slit, a cross-slit or any other suitable slit arrangement that, under differential pressure, allows fluid transport through the disc in either direction, that is, from the bulk formulation to the pre-metering region and from the pre-metering region to the bulk formulation.

The benefits of the elastomeric disc are: such a component takes up minimal space within the valve; and it is symmetrical top to bottom and can therefore be fitted in either top/bottom orientation to allow ease of assembly. The disc may, in addition, feature a thickened outer region to provide more robust handling, insertion and operational stability. The elastomeric disc may also feature a thinner central region in which one or more slits is provided, the thinner central region permitting a greater cross-sectional opening area under opening pressure when the valve refills. Additionally, a second similar a shut-off miniature valve seal may be provided in the outlet path or at the outlet of the pre-metering region. This configuration with two shut-off miniature valve seals effectively isolates the pre-metering region both from the bulk formulation and from the metering chamber in the normal "at rest" position of the metering valve.

The provision of the use of at least a first shut-off miniature valve seal addresses a failure mode which is prevalent in all current suspension-based pMDI devices, namely, turbophoresis, and therefore improves the performance of all suspension-based pMDI devices.

Figure 1:
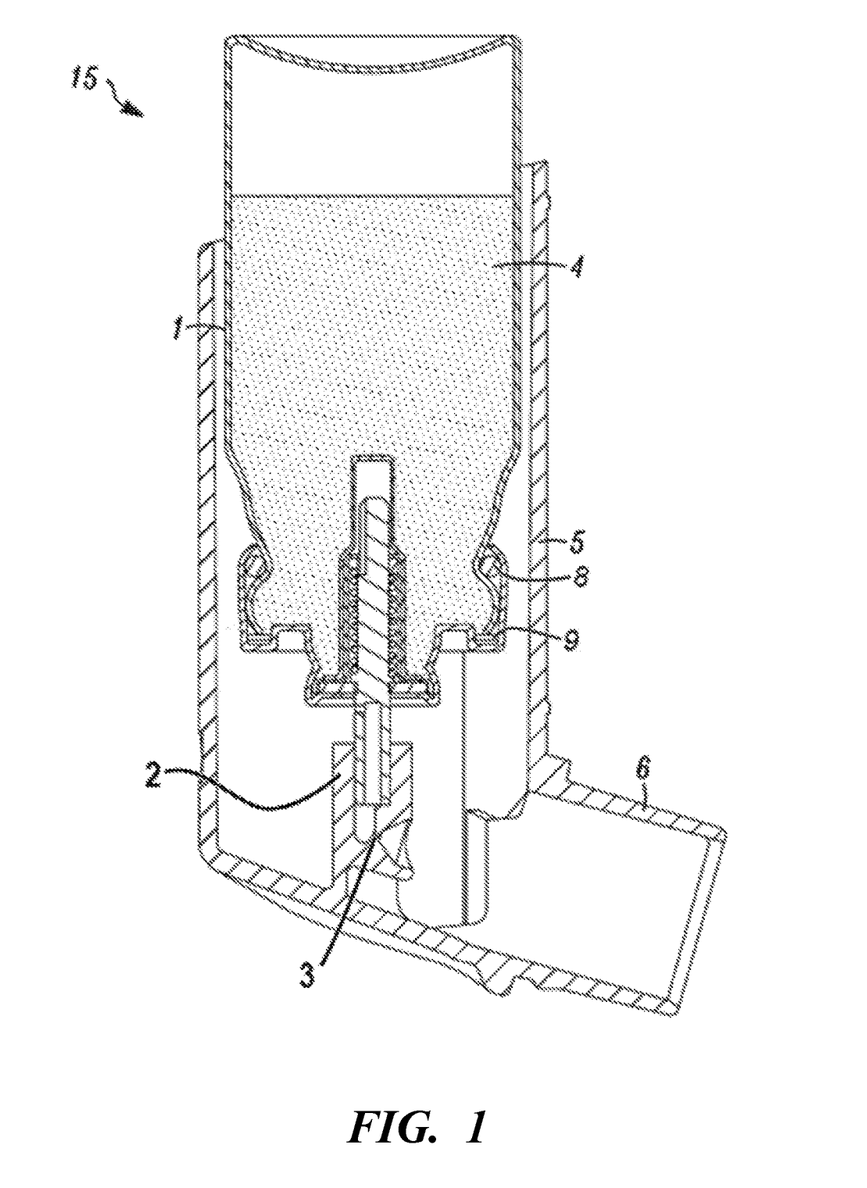
FIG. 1 shows a cross section of pressurized metered dose inhaler of the prior art.

Referring initially to FIG. 1, which shows a pMDI inhaler 15 of the prior art, a valve mechanism is shown mounted on a canister 1 by crimping in place with two seals 8, 9. Typically only one such seal is required. The canister 1 contains bulk formulation 4 of a medicament which is to be dispensed by the pMDI device. This filled canister and valve assembly is inserted into a valve seat 2 of an actuator 5. The valve seat 2 has a nozzle 3 through which the medicament is dispensed. The actuator 5 also includes a mouthpiece 6 through which a user inhales while pressing the canister 1 and actuator 5 towards one another. The mouthpiece 6 is substantially aligned with the nozzle 3 so that the medicament can readily be inhaled by the user.

Figure 2:
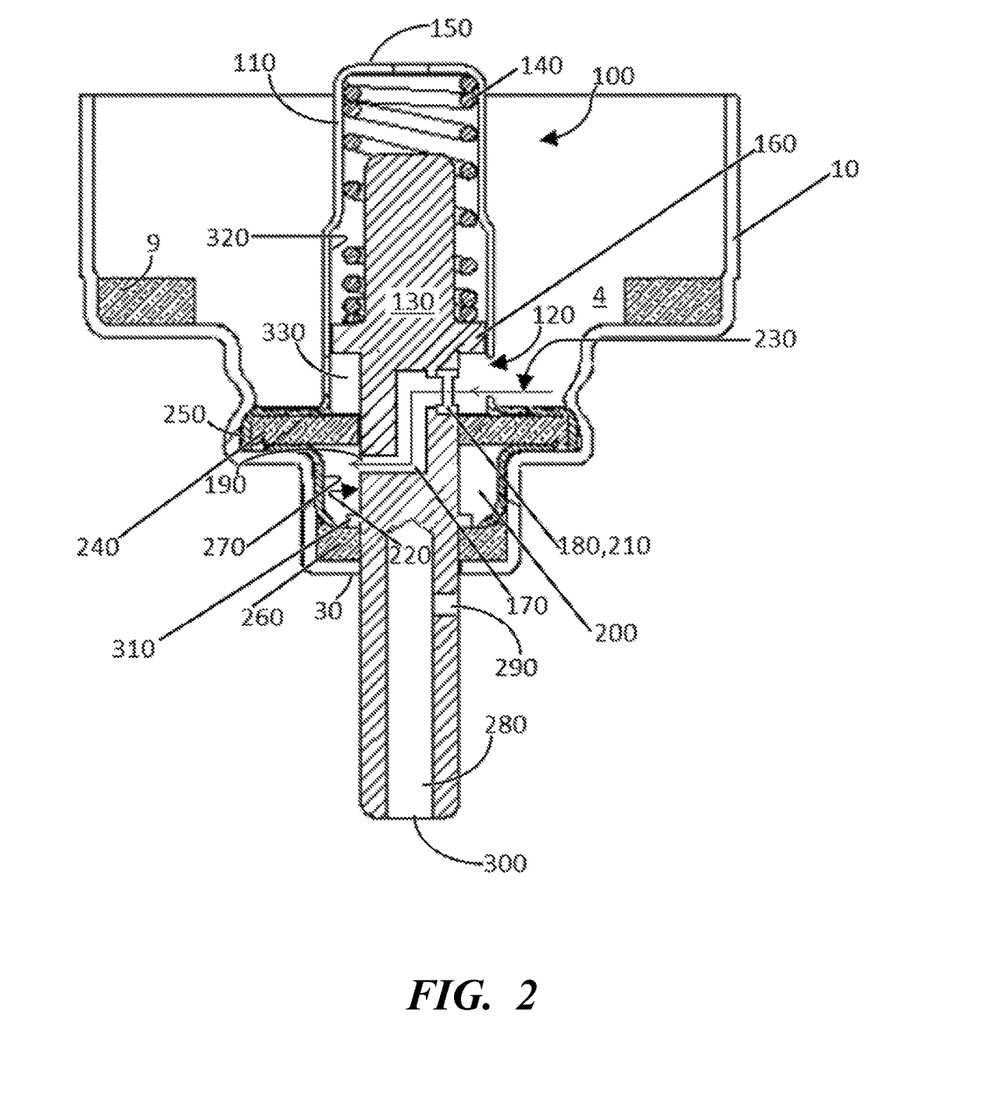
FIG. 2 illustrates a cross section of a valve of a pMDI device, in its rest position, in accordance with one embodiment of the present invention.
Figure 3:
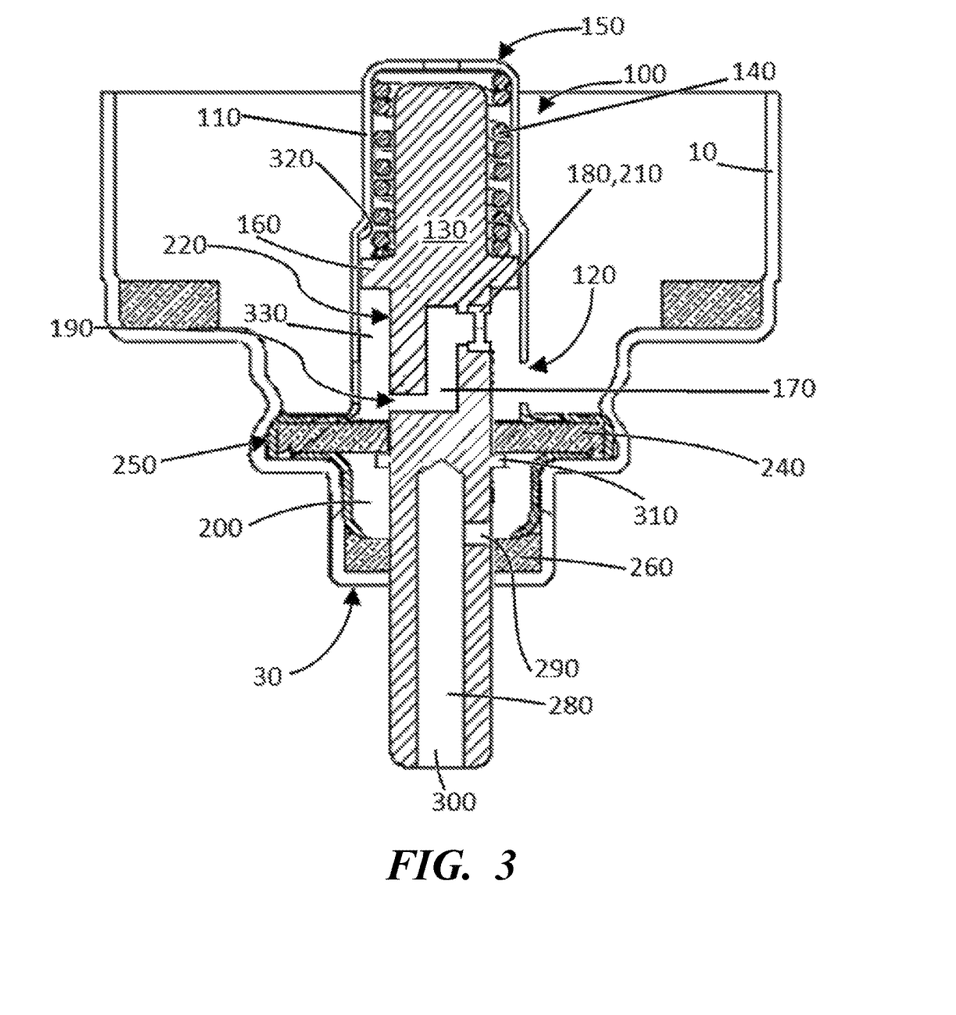
FIG. 3 is similar to FIG. 2 but illustrates the valve in its dispensing position.

Referring now to FIG. 2, the valve mechanism 100 comprises a valve body 110 mounted within a ferrule 10 which provides the means to crimp the valve 100 onto the canister 1 (as shown in FIG. 1). The formulation 4 may enter the valve via an inlet 120 provided in the valve body 110. A valve stem 130 is provided within the valve body 110 and is moveable between at least a first position and a second position with respect to the valve body 110. The first position may comprise an "at rest" position as shown in FIG. 2 and the second position may comprise a "dispensing" position as shown in FIG. 3.

The valve stem 130 is biased to the first position by a spring element 140 which is located within the valve body 110 between an end 150 thereof and a first annular shoulder 160 formed on the valve stem 130. The spring element 140 comprises a compression spring in this embodiment, but it will readily be appreciated that other types of springs can be used to bias the valve stem 130 to the first position.

In the embodiment shown in FIG. 2, the valve stem 130 has a first portion in which a pre-metering region 170 is formed. The pre-metering region 170 has an inlet 180, in fluid communication with the inlet 120 of the valve body 110, and an outlet 190 which is in fluid communication with a substantially annular metering chamber 200 when in the first position. A miniature valve seal 210 as described above is provided at the inlet 180 of the pre-metering region 170 as shown.

In this embodiment, each of the inlet 180 to and the outlet 190 from the pre-metering region 170 is located in a side wall 220 but on diametrically opposite sides thereof and effectively define a substantially "S-shaped" path therebetween. Arrow 230 indicates the flow of fluid from where bulk formulation 4 would be in the valve if mounted to a canister containing the formulation, to the metering chamber 200 through the miniature valve seal 210 at the inlet 180 of the pre-metering region 170, through the pre-metering region 170 itself, and into the metering chamber 200 through the outlet 190. However, it will be appreciated that the inlet 180 and the outlet 190 of the pre-metering region 170 may be formed on the same side of the side wall 220 to define a pre-metering region 170 which effectively define a "C-shaped" path therebetween. The terms "S-shaped" and "C-shaped" are in accordance with the orientation of the valve 100 as shown in FIG. 2. It will be appreciated that other shapes may also be formed in accordance with the orientation of the valve 100 and the positioning of the inlet 180 and the outlet 190 with respect to the side wall 220 of the valve stem 130.

As shown, a first seal element 240 is located around the side wall 220 of the valve stem 130 and is located within an annular portion 250 of the valve body 110, the annular portion of the valve body being retained within the ferrule 10 by any suitable means, for example, by crimping, gluing etc. A second seal element 260 is also located around the side wall 220 of the valve stem 130 and is positioned between a closed end 30 of the ferrule 10 and the valve body 110. The first and second seal elements 240, 260, together with a part 270 of the valve body 110 define the substantially annular metering chamber 200 around the valve stem 130.

The valve stem 130 also has a second portion in which a dispensing channel 280 is formed, the dispensing channel being formed to extend substantially along a longitudinal axis (not shown) of the valve stem 130 from an inlet 290 located in side wall 220 of the valve stem 130 to an outlet 300 located at a distal end thereof.

A second annular shoulder 310 is provided on the side wall 220 in the second portion of the valve stem 130 which serves to define a first position of the valve stem 130 with respect to the valve body 110 as will be described in more detail below.

The first seal element 240 operates to isolate the metering chamber 200 from the pre-metering region 170 when the valve stem 130 is in the second position (FIG. 3) and the second seal element 260 operates to isolate the metering chamber 200 from the dispensing channel 280 in the second portion of the valve stem 130 when in the first position with the second annular shoulder 310 abutting the second seal element 260 as shown.

The distal end of the valve stem 130 is connectable (as shown in FIG. 1) to a valve seat 2 formed in an actuator in which the canister 1 is mounted, the valve seat having a nozzle 3 through which a metered dose is dispensed.

As shown, as the first annular shoulder 160 is effectively guided by an internal wall 320 the valve body 110 during its movement between the first and second positions, an annular space 330 is formed between the valve body 110 and the valve stem 130 and is always in fluid communication with the inlet 120 of the valve body 110. Depending on whether the valve stem 130 is in its first or second position, the volume of the annular space 330 is variable. As shown in FIG. 2, the valve stem 130 is located in its first position with the second annular shoulder 310 abutting the second seal element 260, and the annular space 330 is at its minimum volume.

As shown in FIG. 2 and described above, the miniature valve seal 210 is located at the inlet 180 to the pre-metering region 170. However, it is also possible to locate the miniature valve seal 210 at other positions within an inlet path into the pre-metering region 170.

Turning now to FIG. 3, components previously described bear the same reference numerals and will not be described again in detail.

In FIG. 3, the valve stem 130 is shown in the second or "dispensing" position where the inlet 290 of the dispensing channel 280 is in fluid communication with the metering chamber 200. This allows the metered dose of the medicament to be transferred for inhalation by a patient via the nozzle and mouthpiece (not shown) of an actuator into which the distal end of the valve stem 130 is inserted. In this position, the spring element 140 is compressed against the end 150 of the valve body 110 by the first annular shoulder 160 and the second annular shoulder 310 abuts first seal element 240. Here, fluid flows from the bulk formulation (not shown) into the annular space 330 formed between the valve body 110 and the valve stem 130 through the inlet 120 of the valve body 110. The fluid also flows from the annular space 330 through the pre-metering region 170 and back into the annular space 330 as both the inlet 180 and outlet 190 of the pre-metering region 170 are within the annular space 330.

Here, the valve stem 130 is located in its second position with the second annular shoulder 310 abutting the first seal element 240, and the annular space 330 is at its maximum volume.

Figure 4:
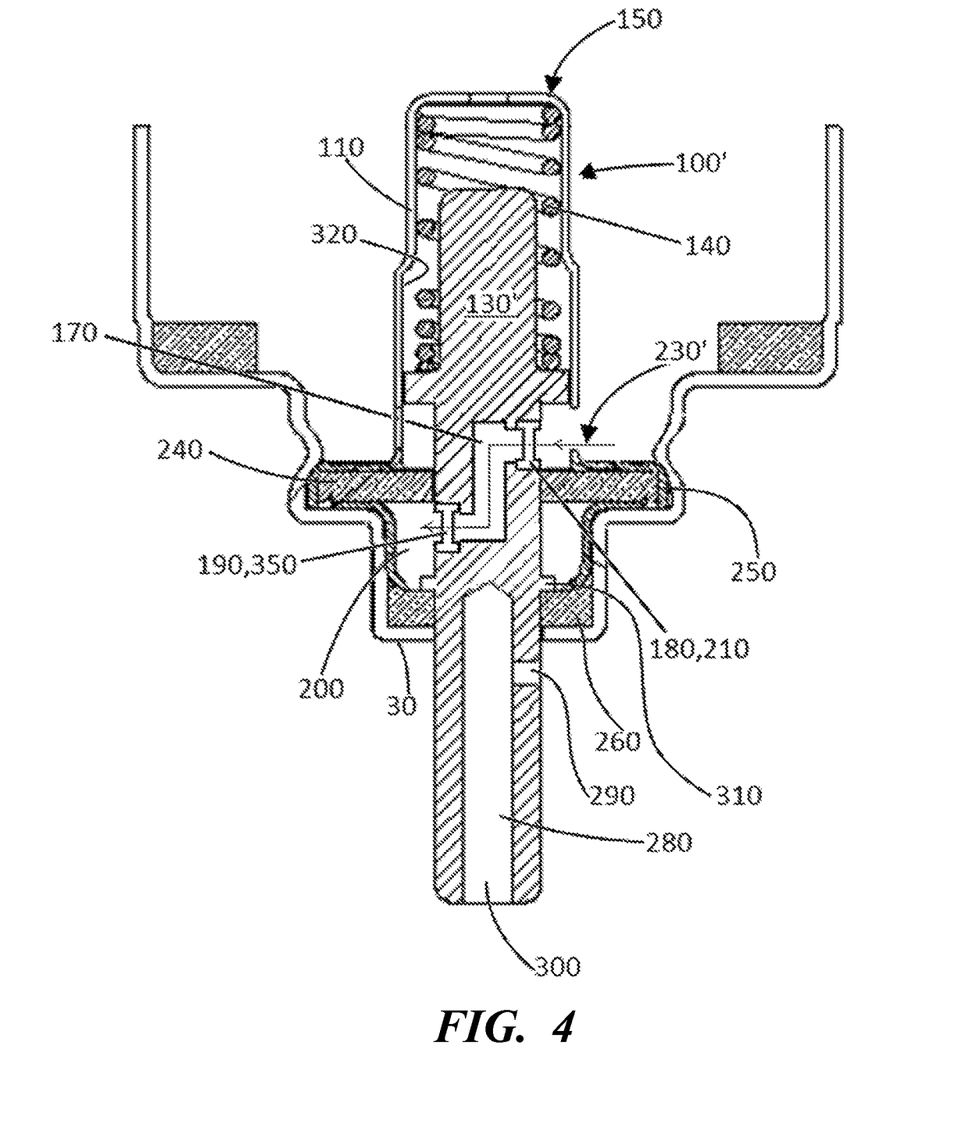
FIG. 4 is similar to FIG. 2 but illustrates a second embodiment of the present invention.

FIG. 4 is similar to FIG. 2 but illustrates the provision of a second miniature valve seal 350 at the outlet 190 of the pre-metering region 170. Components which have previously been described in FIGS. 2 and 3 bear the same reference numerals and will not be described again here in detail. Similar components bear the same reference numeral together with a "prime", for example, valve stem 130' is similar to valve stem 130.

Although the second miniature valve seal 350 is shown as being located at the outlet 190 of the pre-metering region 170, it will readily be appreciated that the second miniature valve seal may be located in an outlet path from the pre-metering region 170.

If the first and second miniature valve seals 210, 350 are not located respectively at the inlet 180 and outlet 190 of the pre-metering region 170, spacers (not shown) may be used to locate them with respect to the inlet 180 and outlet 190. In this way, the first and second miniature valve seals 201, 350 may be located respectively within the inlet path into and the outlet path out of the pre-metering region 170.

The provision of the second miniature valve seal 350, as described above, effectively isolates the pre-metering region from the metering chamber in the first or "at rest" position. Full isolation of the pre-metering region 170 is obtained when two miniature valve seals are implemented, that is, isolation from the bulk formulation (not shown) at the inlet 180 and from the metering chamber 200 at the outlet 190.

It will readily be appreciated that, in any other position than the first or "at rest" position, one of the miniature valve seals may not provide the isolation of the pre-metering region 170 from the bulk composition (not shown) and/or from the metering chamber 200.

Figure 5:
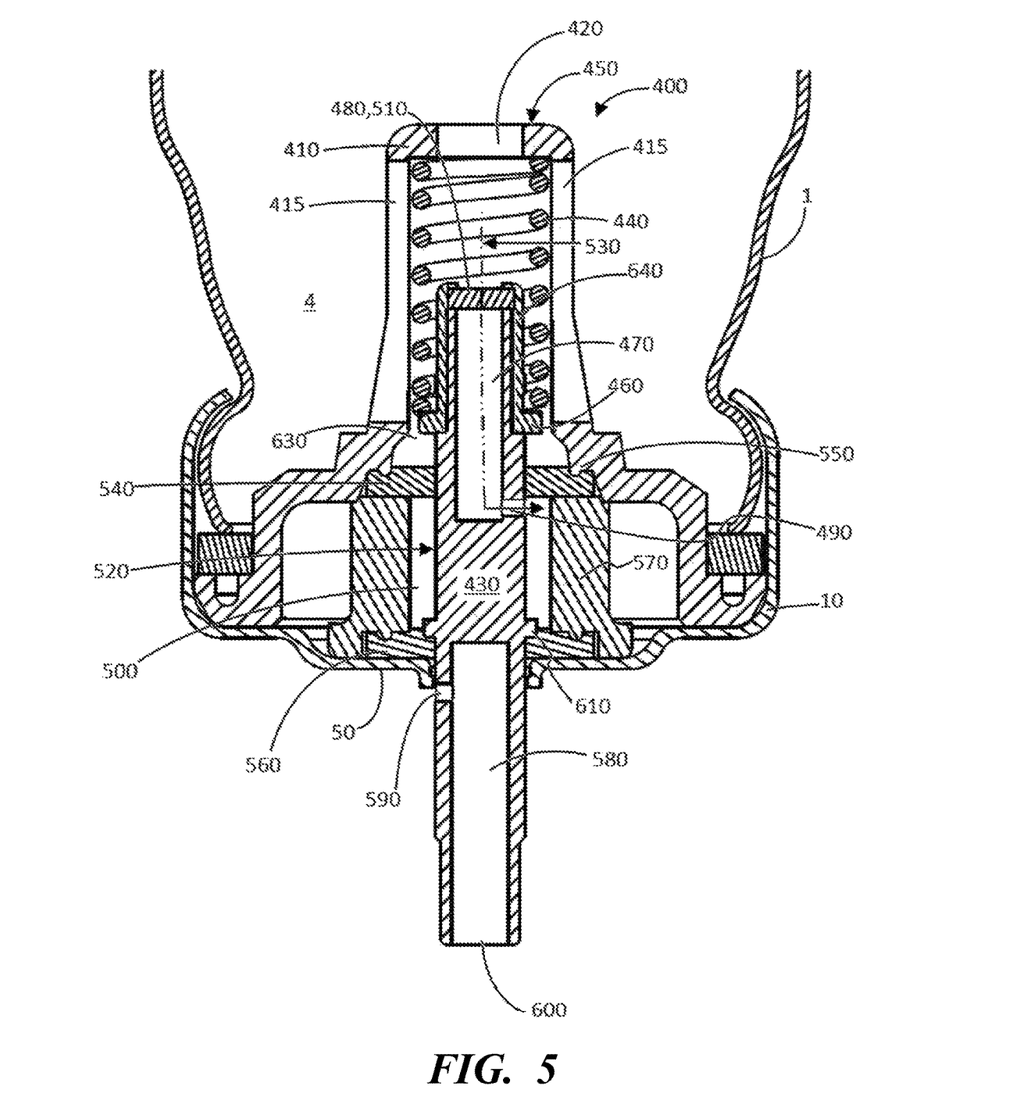
FIG. 5 illustrates a cross section of a valve of a pMDI device crimped onto a canister which is partly shown, in the rest position of the valve, in accordance with a third embodiment of the present invention.

FIG. 5 illustrates another embodiment of a valve mechanism 400 shown mounted on a canister 1 of a pMDI device, in a similar way to that shown in FIG. 1. The canister 1 contains bulk formulation 4 for the medicament which is to be dispensed by the pMDI device. The valve mechanism 400 comprises a valve body 410 mounted within a ferrule 10 and which is connected to the bulk formulation 4 via inlets 415 and 420, through which bulk formulation enters space 630 of the valve body 410. Inlet 415 and inlet 420 are respectively formed in a circumferential wall and at a distal end of the valve body 410. A valve stem 430 is provided within the valve body 410 and is moveable between at least a first position and a second position with respect to the valve body 410. The first position may comprise an "at rest" position as shown in FIG. 5 and the second position may comprise a "dispensing" position (not shown) but as described above with reference to FIG. 3, it corresponds to when medicament is to be dispensed from a metering chamber.

The valve stem 430 is biased to the first position by a spring element 440 which is located within the valve body 410 between an end 450 thereof and a first annular shoulder 460 carried on the valve stem 430. The end 450 defines the inlet 420 in the valve body 410.

In the embodiment shown in FIG. 5, the valve stem 430 has a first portion in which a pre-metering region 470 is formed. The pre-metering region 470 has an inlet 480, in fluid communication with the inlets 415, 420 of the valve body 410, and an outlet 490 which is in fluid communication with a substantially annular metering chamber 500 when in the first position as shown. A miniature valve seal 510 as described above is provided at the inlet 480 of the pre-metering region 470 as shown.

In this embodiment, the inlet 480 to the pre-metering region 470 is located at a proximal end of the valve stem 430 and the outlet 490 from the pre-metering region 470 is located in a side wall 520. In this embodiment, a path through the pre-metering region 470 between the inlet 480 and the outlet 490 effectively defines a substantially "L-shaped" path therebetween. Arrow 530 indicates the flow of fluid from the bulk formulation 4 to the metering chamber 500 through the miniature valve seal 510 at the inlet 480 of the pre-metering region 470, through the pre-metering region 470 itself, and into the metering chamber 500 through the outlet 490. The term "L-shaped" is in accordance with the orientation of the valve 400.

As shown, a first seal element 540 is located around the side wall 520 of the valve stem 430 and is located within an annular portion 550 of the valve body 410, the annular portion of the valve body comprising a recess into which the first seal element 540 is inserted. A second seal element 560 is also located around the side wall 520 of the valve stem 430 and is positioned between a closed end 50 of the ferrule 10 and the valve stem 430. The first and second seal elements 540, 560, together with a part 570 of the valve body 410 define the substantially annular metering chamber 500 around the valve stem 430.

The part 570 of the valve body 410 also operates to retain both the first and second seal elements 540, 560 in their respective positions as shown.

The valve stem 430 also has a second portion in which a dispensing channel 580 is formed, the dispensing channel being formed to extend substantially along a longitudinal axis (not shown) of the valve stem 430 from an inlet 590 located in side wall 520 of the valve stem 430 to an outlet 600 located at a distal end thereof.

A second annular shoulder 610 is provided on the side wall 520 in the second portion of the valve stem 430 which serves to define the first position of the valve stem 430 with respect to the valve body 410 as will be described in more detail below.

The first seal element 540 operates to isolate the metering chamber 500 from the pre-metering region 470 when the valve stem 430 is in the second position (not shown) and the second seal element 560 operates to isolate the metering chamber 500 from the dispensing channel 590 in the second portion of the valve stem 430 when in the first position with the second annular shoulder 610 abutting the second seal element 560 as shown. Although not shown, it will readily be appreciated that the second annular shoulder 610 may abut the first seal element 540 when the valve stem 430 is in the second position.

The distal end of the valve stem 430 is connectable to a valve seat (not shown) formed in an actuator in which the canister 1 is mounted, the valve seat having a nozzle (also not shown) through which a metered dose is dispensed.

As shown, a space 630 is formed between the valve body 410 and the valve stem 430 and is always in fluid communication with the inlets 415, 420 of the valve body 410. Irrespective of whether the valve stem 430 is in its first or second position, the volume of the space 630 is substantially the same.

As shown in FIG. 5 and described above, the miniature valve seal 510 is located at the inlet 480 to the pre-metering region 470. However, it is also possible to locate the miniature valve seal 510 at other positions within an inlet path into the pre-metering region 470.

In the embodiment shown in FIG. 5, the first annular shoulder 460 is not formed directly as a part of the valve stem 430 but is formed on a cap 640 carried at the proximal end of the valve stem 430. It will be appreciated that, in an alternative embodiment (not shown), the first annular shoulder 460 may be formed as part of the valve stem 430.

In the second or "dispensing" position (not shown), the valve stem 430 is pushed towards the end 450 of the valve body 410 against the action of the spring element 440 so that the inlet 590 of the dispensing channel 580 is in fluid communication with the metering chamber 500. This allows the metered dose of the medicament to be transferred for inhalation by a patient via the nozzle and mouthpiece (not shown) of an actuator into which the distal end of the valve stem 430 is inserted.

Figure 6:
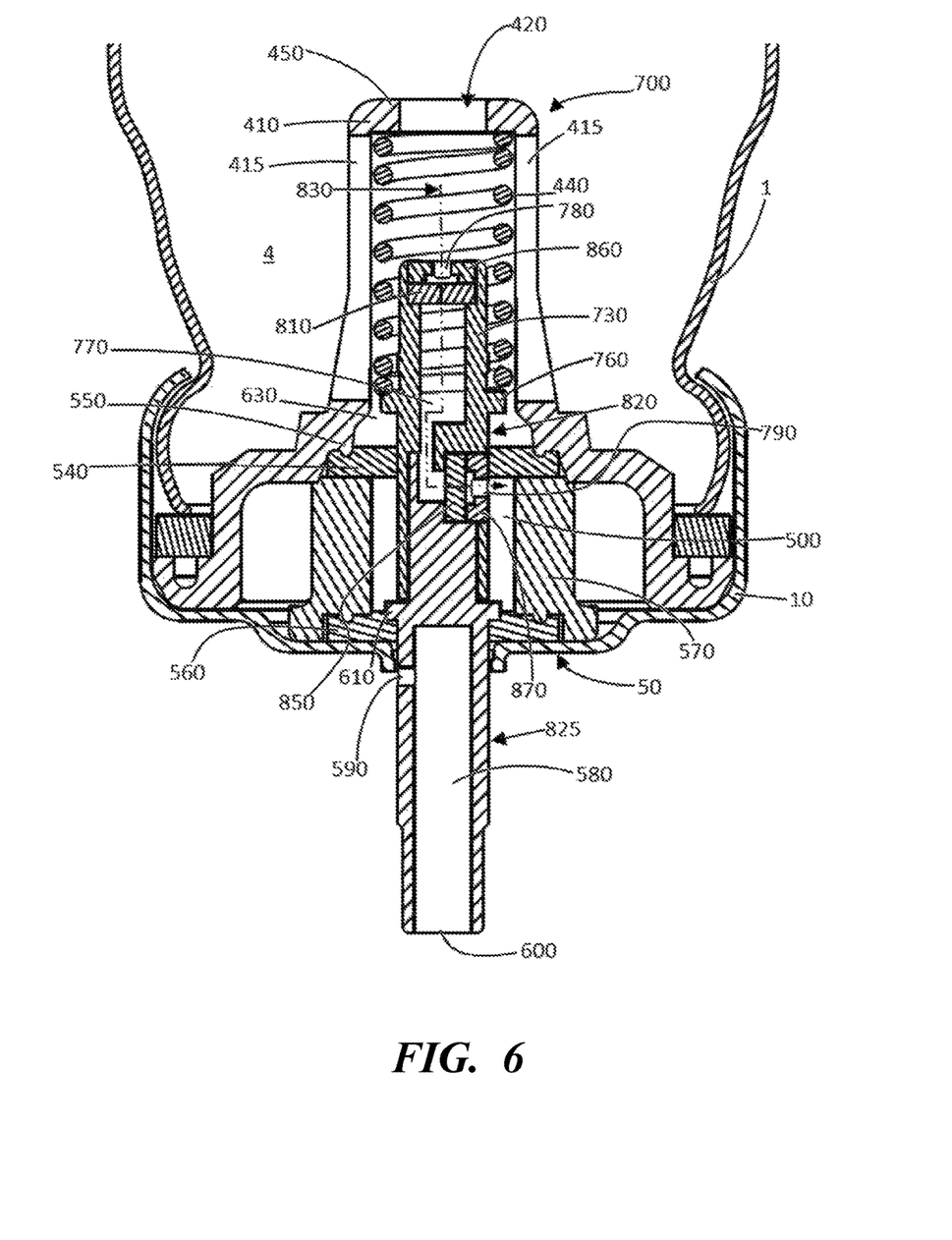
FIG. 6 illustrates a cross section of a valve of a pMDI device crimped onto a canister which is partly shown, in the rest position of the valve, in accordance with a fourth embodiment of the present invention.

In this position, the spring element 440 is compressed against the end 450 of the valve body 410 by the first annular shoulder 460 and the second annular shoulder 610 may abut first seal element 540. Here, fluid flows from the bulk formulation 4 into the space 630 formed between the valve body 410 and the valve stem 430 through the inlets 415, 420 of the valve body 410. Although the volume of the space 630 is substantially the same irrespective of the position of the valve stem 430 within the valve body 410, it will be appreciated that a small change in volume may be experienced due to more of the first portion of valve stem 430 being within the space 630. FIG. 6 is similar to FIG. 5 but illustrates another valve mechanism 700 in which a different valve stem is provided with two miniature valve seals within the pre-metering region. Components which have been described with reference to FIG. 5 bear the same reference numerals and will not be described in detail again here.

Figure 7:
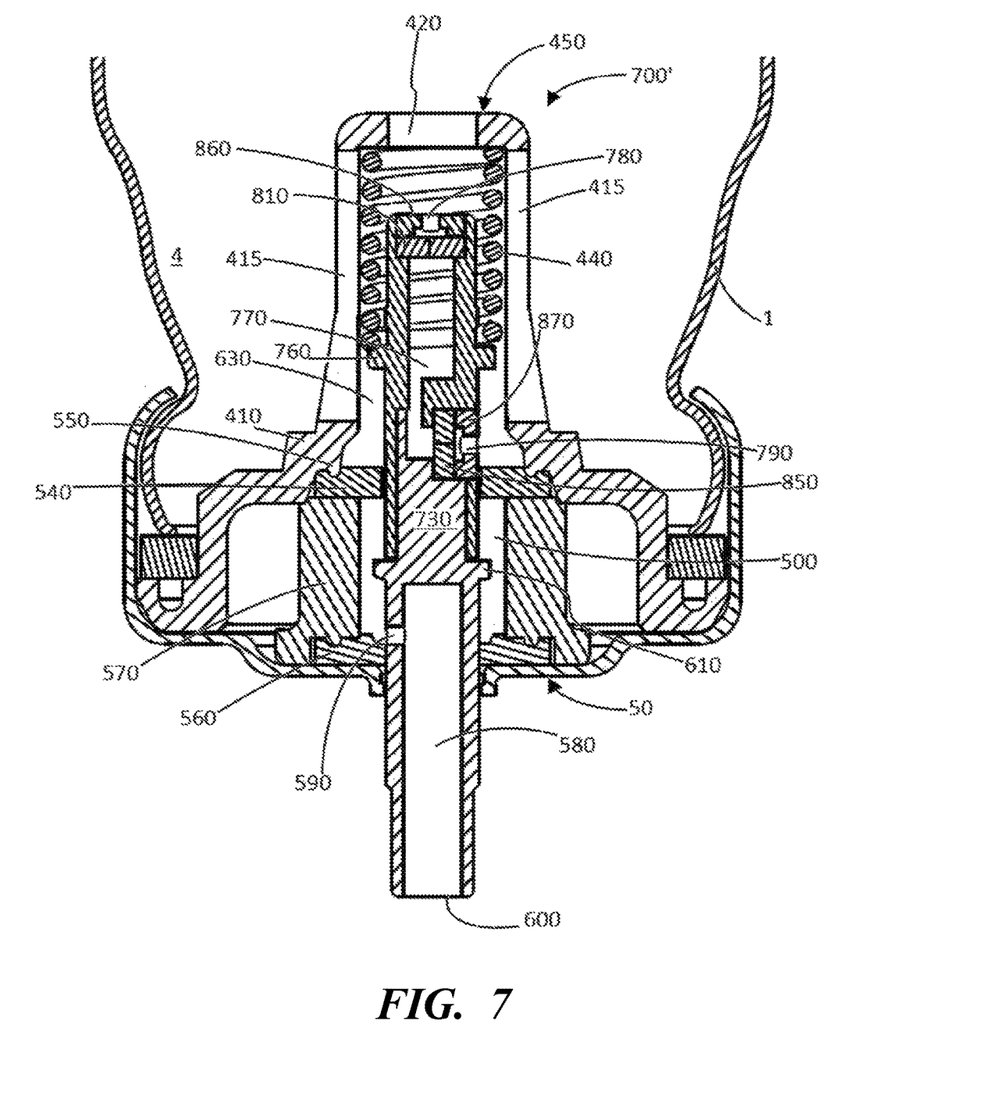
FIG. 7 is similar to FIG. 6 but illustrates the valve in its dispensing position.

The valve mechanism 700 comprises a valve body 410 mounted within the ferrule 10 and which is connected to the bulk formulation 4 via an inlets 415, 420. A valve stem 730 is provided within the valve body 410 and is moveable between at least a first position and a second position with respect to the valve body 410. The first position may comprise an "at rest" position, as shown in FIG. 6, and the second position may comprise a "dispensing" position (as shown in FIG. 7).

The valve stem 730 is biased to the first position by a spring element 440 which is located within the valve body 410 between an end 450 thereof and a first annular shoulder 760 formed on the valve stem 730. In the embodiment shown in FIG. 6, the valve stem 730 has a first portion in which a pre-metering region 770 is formed. The pre-metering region 770 has an inlet 780, in fluid communication with the inlets 415, 420 of the valve body 410, and an outlet 790 which is in fluid communication with a substantially annular metering chamber 500 when in the first position as shown. A miniature valve seal 810 as described above is provided adjacent the inlet 780 of the pre-metering region 770 as shown. In this case, the miniature valve seal 810 is not located at the inlet as described with reference to FIG. 5, but is located in an inlet path from the inlet 780 to the pre-metering region 770.

In this embodiment, the outlet 790 from the pre-metering region 770 is located in a side wall 820 of the valve stem 730. The inlet 780 is located at the proximal end of the valve stem 730. In this embodiment, a path through the pre-metering region 770 between the inlet 780 and the outlet 790 effectively defines a substantially "L-shaped" path therebetween. Arrow 830 indicates the flow of fluid from the bulk formulation 4 to the metering chamber 500 through the miniature valve seal 810 adjacent the inlet 790 of the pre-metering region 770, through the pre-metering region 770 itself, and into the metering chamber 500 through the outlet 790. The term "L-shaped" as used here refers to the orientation of the valve 700 as shown in FIG. 6.

As shown, a first seal element 540 is located around the side wall 820 of the valve stem 730 and is located within an annular portion 550 of the valve body 410, the annular portion of the valve body comprising a recess into which the first seal element 540 is inserted. A second seal element 560 is also located around the side wall 820 of the valve stem 730 and is positioned between a closed end 50 of the ferrule 10 and a part 570 of the valve body 410. The first and second seal elements 540, 560, together with a part 570 of the valve body 410 define the substantially annular metering chamber 500 around the valve stem 430.

The part 570 of the valve body 410 also operates to retain both the first and second seal elements 540, 560 in their respective positions as shown.

The valve stem 730 also has a second portion in which a dispensing channel 580 is formed, the dispensing channel being formed to extend substantially along a longitudinal axis (not shown) of the valve stem 730 from an inlet 590 located in side wall 820 of the valve stem 730 to an outlet 600 located at a distal end thereof.

A second annular shoulder 610 is provided on the side wall 825 in the second portion of the valve stem 730 which serves to define the first position of the valve stem 730 with respect to the valve body 410.

The first seal element 540 operates to isolate the metering chamber 500 from the pre-metering region 770 when the valve stem 730 is in the second position (not shown) and the second seal element 560 operates to isolate the metering chamber 500 from the dispensing channel 580 in the second portion of the valve stem 730 when in the first position with the second annular shoulder 610 abutting the second seal element 560 as shown.

As before, the distal end of the valve stem 730 is connectable to a valve seat (not shown) formed in an actuator in which the canister 1 is mounted, the valve seat having a nozzle (also not shown) through which a metered dose is dispensed.

As shown and described above, a space 630 is formed between the valve body 410 and the valve stem 730 and is always in fluid communication with the inlets 415, 420 of the valve body 410. Irrespective of whether the valve stem 730 is in its first or second position, the volume of the space 630 is substantially the same.

As shown in FIG. 6 and described above, the miniature valve seal 810 is located within the pre-metering region 770 and adjacent the inlet 780 thereto, that is, in an inlet path to the pre-metering region 770. However, it is also possible to locate the miniature valve seal 710 at the inlet 780 into the pre-metering region 770 in a similar way to that described for the embodiments shown in FIGS. 2 to 4.

In the second or "dispensing" position as shown in FIG. 7, the valve stem 730 is pushed towards the end 450 of the valve body 410 against the action of the spring element 440 so that the inlet 590 of the dispensing channel 580 is in fluid communication with the metering chamber 500. This allows the metered dose of the medicament to be transferred for inhalation by a patient via the nozzle and mouthpiece (not shown) of an actuator into which the distal end of the valve stem 730 is inserted.

In this position, the spring element 440 is compressed against the end 450 of the valve body 410 by the first annular shoulder 760. Here, fluid flows from the bulk formulation 4 into the space 630 formed between the valve body 410 and the valve stem 730 through the inlets 415, 420 of the valve body 410. Here, the valve stem 730 is located in its second position in which the second annular shoulder 610 may abut the first seal element 540. Although the volume of the space 630 is substantially the same irrespective of the position of the valve stem 730 within the valve body 410, it will be appreciated that a small change in volume may be experienced due to more of the first portion of valve stem 730 being within the space 630.

As shown in FIGS. 6 and 7, a second miniature valve seal 850 is located adjacent the outlet 790 to the pre-metering region 770. The first and second miniature valve seals 810, 850 are located within the pre-metering region 770 with the first miniature valve seal 810 being spaced from the inlet 780 by a first spacer element 860 and the second miniature valve seal 850 being spaced from the outlet 790 by a second spacer element 870. The first and second spacer elements 860, 870 have apertures in their central regions which are aligned with respective ones of the inlet 780 and the outlet 790. Preferably, the exposed surface of each spacer is flush with the corresponding side wall 820, 825 of the valve stem 730.

Although both miniature valve seals are located within the pre-metering region in an inlet path and an outlet path, it will readily be appreciated that, as an alternative, only one of these valve seals may be located within the pre-metering region with the other being at the inlet as described above with reference to FIG. 5 or at the outlet (not shown). As further options, either or both miniature valve seals may be located at the corresponding inlet or outlet (also not shown).

Figure 8:
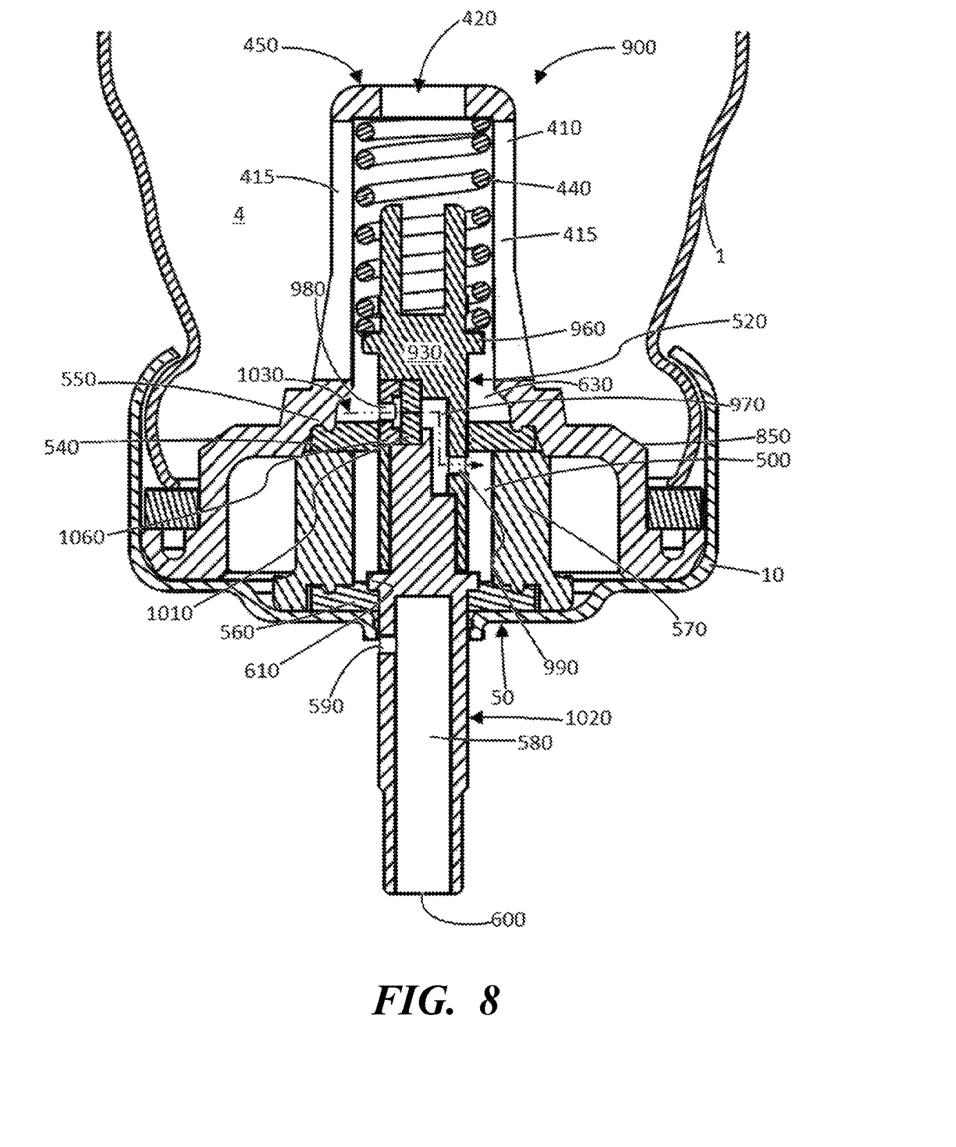
FIG. 8 illustrates a schematic cross section of a valve of a pMDI device crimped onto a canister which is partly shown, in the rest position of the valve, in accordance with a fifth embodiment of the present invention.

FIG. 8 illustrates another valve mechanism 900, similar to that described above with reference to FIG. 5, in which the inlet to the pre-metering region is located in a different position. Components which have been described with reference to FIG. 5 bear the same reference numerals.

The valve mechanism 900 comprises a valve body 410 mounted within the ferrule 10 and which is connected to the bulk formulation 4 via an inlet 420. A valve stem 930 is provided within the valve body 410 and is moveable between at least a first position and a second position with respect to the valve body 410. The first position may comprise an "at rest" position as shown and described above, and the second position may comprise a "dispensing" position (not shown) but as described above with reference to FIGS. 3 and 7, it corresponds to when medicament is to be dispensed from a metering chamber.

The valve stem 930 is biased to the first position by a spring element 440 which is located within the valve body 410 between an end 450 thereof and a first annular shoulder 960 formed on the valve stem 930. The valve stem 930 has a first portion in which a pre-metering region 970 is formed, the pre-metering region 970 having an inlet 980, in fluid communication with the inlet 420 of the valve body 410, and an outlet 990 which is in fluid communication with a substantially annular metering chamber 500 when in the first position as shown and as described above.

A miniature valve seal 1010 as described above is provided adjacent the inlet 980 of the pre-metering region 970 as shown. In this case, the miniature valve seal 1010 is not located at the inlet as described with reference to FIG. 5 but is located in an inlet path from the inlet 980 to the pre-metering region 970.

In this embodiment, the inlet 980 to and the outlet 990 from the pre-metering region 970 is located in a side wall 1020 of the valve stem 930. In this embodiment, a path through the pre-metering region 970 between the inlet 980 and the outlet 990 effectively defines a substantially "Z-shaped" path therebetween. Arrow 1030 indicates the flow of fluid from the bulk formulation 4 to the metering chamber 500 through the miniature valve seal 1010 adjacent the inlet 980 of the pre-metering region 970, through the pre-metering region 970 itself, and into the metering chamber 500 through the outlet 990. The term "Z-shaped" as used herein refers to the orientation of the valve mechanism 900.

As shown, a first seal element 540 is located around the side wall 520 of the valve stem 930 and is located within an annular portion 550 of the valve body 410, the annular portion of the valve body comprising a recess into which the first seal element 540 is inserted. A second seal element 560 is also located around the side wall 1020 of the valve stem 930 and is positioned between a closed end 50 of the ferrule 10 and the valve stem 930. The first and second seal elements 540, 560, together with a part 570 of the valve body 410 define the substantially annular metering chamber 500 around the valve stem 930.

The part 570 of the valve body 410 also operates to retain both the first and second seal elements 540, 560 in their respective positions as shown.

The valve stem 930 also has a second portion in which a dispensing channel 580 is formed, the dispensing channel being formed to extend substantially along a longitudinal axis (not shown) of the valve stem 930 from an inlet 590 located in side wall 1020 of the valve stem 930 to an outlet 600 located at a distal end thereof.

A second annular shoulder 610 is provided on the side wall 1020 in the second portion of the valve stem 930 which serves to define the first position of the valve stem 930 with respect to the valve body 410, by limiting the outward movement of the valve stem.

The first seal element 540 operates to isolate the metering chamber 500 from the pre-metering region 970 when the valve stem 930 is in the second position (not shown) and the second seal element 560 operates to isolate the metering chamber 500 from the dispensing channel 590 in the second portion of the valve stem 930 when in the first position with the second annular shoulder 610 abutting the second seal element 560 as shown. Although not shown, it will readily be appreciated that the second annular shoulder 610 may abut the first seal element 540 when the valve stem 930 is in the second position.

As before, the distal end of the valve stem 930 is connectable to a valve seat (not shown) formed in an actuator in which the canister 1 is mounted, the valve seat having a nozzle (also not shown) through which a metered dose is dispensed.

As shown and described above with reference to FIG. 5, a space 630 is formed between the valve body 410 and the valve stem 930 and is always in fluid communication with the inlet 420 of the valve body 410. Irrespective of whether the valve stem 930 is in its first or second position, the volume of the space 630 is substantially the same.

As shown in FIG. 8 and described above, the miniature valve seal 1010 is located within the pre-metering region 970 and adjacent the inlet 980 thereto, that is, in an inlet path to the pre-metering region 970. A spacer element 1060 is located at the inlet 980 to space the miniature valve seal 1010 therefrom. As described above, the spacer element 1060 has an aperture in its central region which is aligned with the inlet 980 of the pre-metering region 970. However, it is also possible to locate the miniature valve seal 1010 at the inlet 980 into the pre-metering region 970 in a similar way to that described for the embodiments shown in FIGS. 2 to 4.

In the second or "dispensing" position (not shown), the valve stem 930 is pushed towards the end 450 of the valve body 410 against the action of the spring element 440 so that the inlet 590 of the dispensing channel 580 is in fluid communication with the metering chamber 500. This allows the metered dose of the medicament to be transferred for inhalation by a patient via the nozzle and mouthpiece (not shown) of an actuator into which the distal end of the valve stem 930 is inserted.

In this position, the spring element 440 is compressed against the end 450 of the valve body 410 by the first annular shoulder 960 and the second annular shoulder 610 may abut first seal element 540. Here, fluid flows from the bulk formulation 4 into the space 630 formed between the valve body 410 and the valve stem 930 through the inlets 415, 420 of the valve body 410. Although the volume of the space 630 is substantially the same irrespective of the position of the valve stem 930 within the valve body 410, it will be appreciated that a small change in volume may be experienced due to more of the first portion of valve stem 930 being within the space 630.

In another embodiment (not shown), a second miniature valve seal may be located at the outlet 990 to the pre-metering region 970 in a similar manner to that described with reference to the embodiment shown in FIG. 4 above.

Although not specifically described above with respect to the embodiments shown in FIGS. 5 to 8, the valve stem in each case comprises a plurality of component parts which are joined together to form the illustrated valve stem profiles. Alternatively, not shown, the valve stem in each case may comprise an integral component having appropriate openings to form the inlet and the outlet for respective pre-metering regions.

In addition, although the miniature valve seals have been described as being separate to associated spacer elements, it will readily be appreciated that the seals may be formed integrally with, or as part of, the spacer elements. Alternatively, the miniature valve seals may be co-moulded with the valve stem.

Although the embodiments shown in FIGS. 5 to 8 illustrate the presence of an internal wall 570, it will readily be appreciated that the wall of the valve body 410 may be suitably shaped to delimit the metering chamber 500. In the latter case, other means may need to be provided to retain the first and second seal elements 540, 560 in place within the valve body 410.

The invention claimed is:

1. A metering valve comprising:
   a housing;
   a valve body mounted in the housing, the valve body having an inlet;
   a valve stem moveable within the valve body between at least a first position and a second position with respect to the valve body;
   a return member located within the valve body and being operable for biasing the valve stem to the first position;
   a pre-metering region formed within a first portion of the valve stem, the pre-metering region including an inlet port and an outlet port, the inlet port being connected to the inlet of the valve body;
   a metering chamber formed between the valve stem and the valve housing, the metering chamber being connectable to the outlet port of the pre-metering region;
   a first dose retention element positioned in an inlet path to the pre-metering region and being operable for retaining a measured dose within the pre-metering region, the first dose retention element providing fluid transport in both directions therethrough; and
   a dispensing channel formed within a second portion of the valve stem, the dispensing channel having a dispensing inlet and a dispensing outlet, the dispensing inlet being connectable to the metering chamber in the second position.

2. A metering valve according to claim 1, wherein the first dose retention member is located at an entrance to the pre-metering region, the entrance being substantially adjacent the inlet port.

3. A metering valve according to claim 1, wherein the outlet port comprises an opening in a circumferential wall of the valve stem.

4. A metering valve according to claim 1, wherein the inlet port comprises an opening at a proximal end of the valve stem.

5. A metering valve according to claim 4, wherein the first dose retention member has an axis which is substantially aligned with the inlet port.

6. A metering valve according to claim 4, wherein the first dose retention member has an axis which is aligned to be substantially parallel with the outlet port.

7. A metering valve according to claim 1, wherein the inlet port comprises an opening in a circumferential wall of the valve stem disposed at a distance from the outlet port.

8. A metering valve according to claim 7, wherein the first dose retention member has an axis which is substantially aligned with the inlet port.

9. A metering valve according to claim 7, wherein the first dose retention member has an axis which is aligned to be substantially parallel with the outlet port.

10. A metering valve according to claim 1, wherein the first dose retention member comprises an elastomeric disc with at least one re-sealable slit located in a central region thereof.

11. A metering valve according to claim 10, wherein the elastomeric disc has a circumferential region which is thicker than the central region thereof.

12. A metering valve according to claim 1, further comprising a second dose retention member positioned in an outlet path of the pre-metering region.

13. A metering valve according to claim 12, wherein the second dose retention member is located at an exit to the pre-metering region.

14. A metering valve according to claim 12, wherein the second dose second retention member has an axis which is substantially aligned with the outlet port.

15. A metering valve according to claim 12, wherein the second dose retention member comprises an elastomeric disc with at least one re-sealable slit located in a central region thereof.

16. A metering valve according to claim 15, wherein the elastomeric disc has a circumferential region which is thicker than the central region thereof.

17. A metering valve according to claim 15, wherein the second dose retention member is substantially identical to the first dose retention member.

\* \* \* \* \*